United States Patent
Kamada et al.

(10) Patent No.: US 10,759,672 B2
(45) Date of Patent: Sep. 1, 2020

(54) BARIUM SULFATE SPHERICAL COMPOSITE POWDER AND METHOD FOR PRODUCING SAME

(71) Applicant: Sakai Chemical Industry Co., Ltd., Sakai-shi, Osaka (JP)

(72) Inventors: Satoshi Kamada, Osaka (JP); Takuro Ashida, Osaka (JP)

(73) Assignee: SAKAI CHEMICAL INDUSTRY CO., LTD., Osaka (JP)

( * ) Notice: Subject to any disclaimer, the term of this patent is extended or adjusted under 35 U.S.C. 154(b) by 0 days.

(21) Appl. No.: 16/487,740

(22) PCT Filed: Feb. 7, 2018

(86) PCT No.: PCT/JP2018/004210
§ 371 (c)(1),
(2) Date: Aug. 21, 2019

(87) PCT Pub. No.: WO2018/155185
PCT Pub. Date: Aug. 30, 2018

(65) Prior Publication Data
US 2019/0375652 A1 Dec. 12, 2019

(30) Foreign Application Priority Data

Feb. 24, 2017 (JP) ................................. 2017-033656
May 29, 2017 (JP) ................................. 2017-105915

(51) Int. Cl.
| | | |
|---|---|---|
| C01F 11/46 | (2006.01) | |
| C09C 1/30 | (2006.01) | |
| A61K 8/23 | (2006.01) | |

(52) U.S. Cl.
CPC .............. *C01F 11/462* (2013.01); *A61K 8/23* (2013.01); *C09C 1/30* (2013.01); *C01P 2004/03* (2013.01); *C01P 2004/32* (2013.01); *C01P 2004/61* (2013.01); *C01P 2004/80* (2013.01)

(58) Field of Classification Search
CPC ... A61Q 1/10; A61Q 1/08; A61Q 1/04; A61Q 1/02; C01P 2004/32; C01P 2004/03; C01P 2004/62; C01P 2004/61; C01P 2004/80; C01P 2002/54; C01B 33/18; A61K 8/23; A61K 8/2513; C09C 1/027; C09C 1/0081; C01F 11/00; C01F 11/462
See application file for complete search history.

(56) References Cited

U.S. PATENT DOCUMENTS

| | | | | | |
|---|---|---|---|---|---|
| 2,958,578 | A | * | 11/1960 | Baker | A01N 25/08 423/326 |
| 4,505,755 | A | * | 3/1985 | Shinozuka | C09C 1/027 106/431 |
| 5,340,582 | A | * | 8/1994 | Sugasawa | A61K 8/0254 106/461 |
| 5,380,360 | A | * | 1/1995 | Noguchi | A61Q 1/02 106/415 |
| 6,194,070 | B1 | * | 2/2001 | Lynch | C23C 30/00 428/405 |
| 9,855,197 | B2 | * | 1/2018 | Itagaki | A61K 8/27 |
| 2003/0012752 | A1 | * | 1/2003 | Bara | A61Q 1/04 424/63 |
| 2013/0172599 | A1 | | 7/2013 | Suzuki et al. | |

FOREIGN PATENT DOCUMENTS

| | | | | | |
|---|---|---|---|---|---|
| CN | 107746068 | A | * | 3/2018 | ............. B82Y 30/00 |
| JP | 04309566 | A | * | 11/1992 | ............... C09C 1/02 |
| JP | 8-225316 | | | 9/1996 | |
| JP | 8-283124 | | | 10/1996 | |
| JP | 2014-088351 | | | 5/2014 | |
| JP | 2015-113306 | | | 6/2015 | |
| JP | 2016-199454 | | | 12/2016 | |
| WO | 2012/035637 | | | 3/2012 | |
| WO | WO 2017 111145 | A1 | * | 6/2017 | ............. C01F 11/46 |

\* cited by examiner

*Primary Examiner* — Timothy C Vanoy
(74) *Attorney, Agent, or Firm* — Hamre, Schumann, Mueller & Larson, P.C.

(57) ABSTRACT

The present invention provides a barium sulfate spherical composite powder that has significantly high strength and excellent texture, and achieves high haze while maintaining high total light transmittance, and a method for producing such a composite powder. The present invention relates to a method for producing a barium sulfate spherical composite powder, which is a method for producing a spherical composite powder of barium sulfate and silica, the method comprising the steps of (1) preparing a slurry containing particulate barium sulfate and a silica sol, (2) spray-drying the slurry, and (3) firing a dry substance obtained in the step (2).

6 Claims, 3 Drawing Sheets

Experimental Example 1

(a) SEM image (×5000)

(b) Cross-sectional COMPO image of particle (×10000)

(c) Cross-sectional SEM image of particle (×10000)

(d) Cross-sectional elemental mapping of particle : Si (e) Cross-sectional elemental mapping of particle : Ba (a) Experimental Example 2 (×5000)

(b) Experimental Example 4 (×5000)

(c) Experimental Example 5 (×5000)

(d) Experimental Example 6 (×5000)

(e) Experimental Example 7 (×5000)

(f) Experimental Example 8 (×10000)

(a) Experimental Example 2 (×10000)

(b) Experimental Example 5 (×10000)

(c) Experimental Example 6 (×10000)

BARIUM SULFATE SPHERICAL COMPOSITE POWDER AND METHOD FOR PRODUCING SAME

TECHNICAL FIELD

The present invention relates to a barium sulfate spherical composite powder and methods for producing the same.

BACKGROUND ART

Inorganic particles include particles of various shapes. For example, spherical particles are used in various applications such as cosmetic products and coating materials. In these applications, a spherical shape is advantageous for matting or increasing light diffusion to give a composition having high haze. In particular, since spherical particles easily glide on the skin, they are incorporated in cosmetic products so as to enhance smoothness, softness, ease of spreading, and other textures. The spherical particles are, for example, barium sulfate particles that are inexpensive, easily chemically synthesized, and less soluble in acids and alkalis, and have low solubility in water and organic solvents. Patent Literature 1, Patent Literature 2, and Patent Literature 3 disclose conventional spherical barium sulfate.

CITATION LIST

Patent Literature

Patent Literature 1: JP 2016-199454 A
Patent Literature 2: JP H08-283124 A
Patent Literature 3: JP H08-225316 A

SUMMARY OF INVENTION

Technical Problem

Patent Literature 1 achieves spherical barium sulfate that has low specific density, high sphericity, sufficient strength, excellent smoothness, excellent safety, and very good texture and is useful for various applications such as cosmetic products. However, as a result of intensive studies made by the present inventors, such spherical barium sulfate was found to still have room for improvement in strength and texture (see Experimental Example 5 described later). Also, in recent years, cosmetic products are required to have not only good texture but also an excellent soft focus effect of making wrinkles and pores less noticeable by a light scattering effect. For such demands, haze needs to be increased while high total light transmittance is maintained. Patent Literature 2 and Patent Literature 3 also disclose spherical barium sulfate, which however has a problem of insufficient haze (see Experimental Example 8 described later).

In view of the current state of the art described above, the present invention aims to provide a barium sulfate spherical composite powder that has significantly high strength and excellent texture and achieves high haze while maintaining high total light transmittance, and also aims to provide a method for producing such a composite powder.

Solution to Problem

The present inventors have made extensive studies on spherical barium sulfate and have found that the spherical barium sulfate disclosed in Patent Literature 1, which has excellent properties, has room for improvement in strength or texture as described above and also has room to achieve high haze while maintaining high total light transmittance. The present inventors have found that a spherical composite powder of barium sulfate and silica produced by preparing a slurry containing particulate barium sulfate and a silica sol, spray-drying the slurry, followed by firing has significantly higher particle strength and better texture than conventional spherical barium sulfate. This spherical composite powder also has significantly higher haze than conventional spherical barium sulfate or common barium sulfate whose surface is treated with silica. Thus, the spherical composite powder incorporated in a cosmetic product exhibits a very high soft focus effect. Here, it is usually understood that the haze of a composite of silica and barium sulfate is lower than that of barium sulfate from the technical common knowledge that the refractive index of silica is lower than the refractive index of barium sulfate. Thus, it can be said that the spherical composite powder, i.e. a composite of barium sulfate and silica, which achieves high haze while maintaining high total light transmittance exerts a qualitatively different effect which is unpredictable from conventional understanding. Thus, they have arrived at an admirable solution to the problem, completing the present invention.

That is the present invention relates to a method for producing a barium sulfate spherical composite powder, which is a method for producing a spherical composite powder of barium sulfate and silica, the method comprising the steps of:

(1) preparing a slurry containing particulate barium sulfate and a silica sol;

(2) spray-drying the slurry; and (3) firing a dry substance obtained in the step (2).

The particulate barium sulfate and the silica in the slurry preferably have a mass ratio ($BaSO_4/SiO_2$) of 99/1 to 55/45.

The firing in the step (3) is preferably performed at a firing temperature of 400° C. to 1000° C.

The present invention also relates to a barium sulfate spherical composite powder which is a spherical composite powder comprising barium sulfate and silica,
the composite powder having
an average particle size of 0.5 to 100 μm,
a haze of 50% or more, and
a silica content of 1 to 45% by mass.

The barium sulfate spherical composite powder preferably further contains a layer surface-treated with a water-repellent organic compound.

The present invention also relates to a cosmetic product comprising the barium sulfate spherical composite powder.

Advantageous Effects of Invention

The production method of the present invention having the above-described features can provide a barium sulfate spherical composite powder having significantly high strength and excellent texture and achieving high haze while maintaining high total light transmittance. Also, the barium sulfate spherical composite powder obtainable by the production method of the present invention and the barium sulfate spherical composite powder of the present invention exhibit a high soft focus effect when they are each incorporated in a cosmetic product. Thus, they are useful particularly for materials of cosmetic products and also useful for medicines, quasi-drugs, radiation shielding materials, coating materials, resin materials, catalysts, toners for printing, lubricants, and other products.

DESCRIPTION OF EMBODIMENTS

Figure 1:
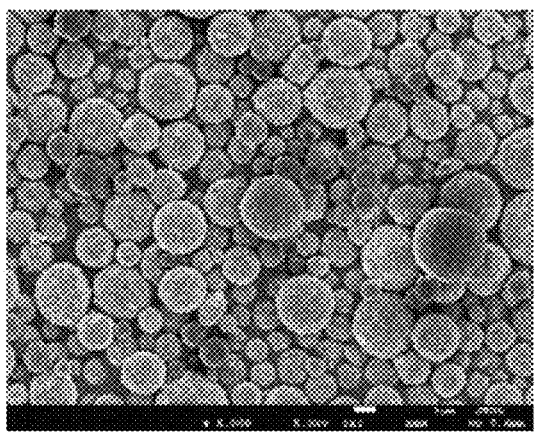
FIG. 1 illustrates micrographs of powders obtained in Experimental Example 1 observed with a scanning electron microscope (SEM). A micrograph (a) is a SEM image taken at a magnification of 5000. Micrographs (b) to (e) are cross-sectional micrographs of particles obtained by cross-section polishing (CP treatment) respectively taken at a magnification of 10000. Specifically, the micrograph (b) is a cross-sectional backscattered electron composition image (COMPO image) of a particle, the micrograph (c) is a cross-sectional SEM image of a particle, the micrograph (d) is a cross-sectional elemental mapping of silicon (Si) in a particle obtained by an energy dispersion X-ray spectroscope (EDS), and the micrograph (e) is a cross-sectional elemental mapping of barium (Ba) in a particle obtained by an EDS.
Figure 1:
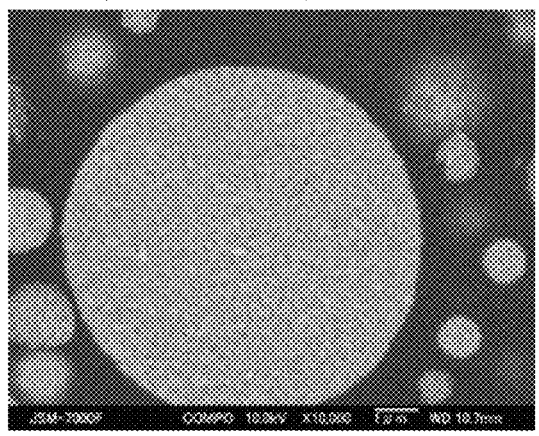
Figure 1:
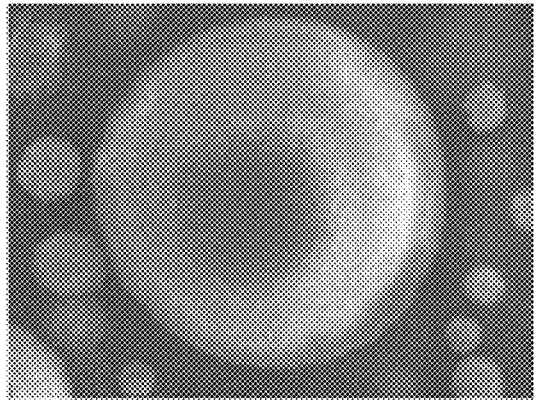
Figure 1:
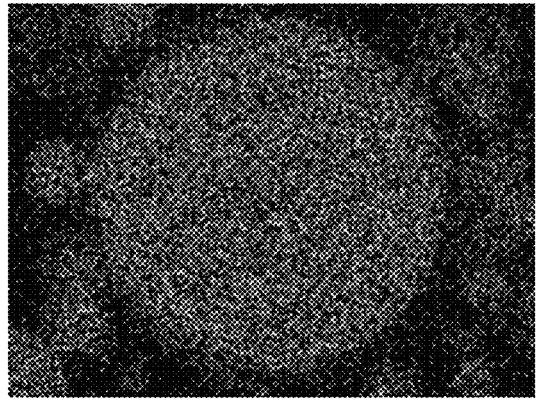
Figure 1:
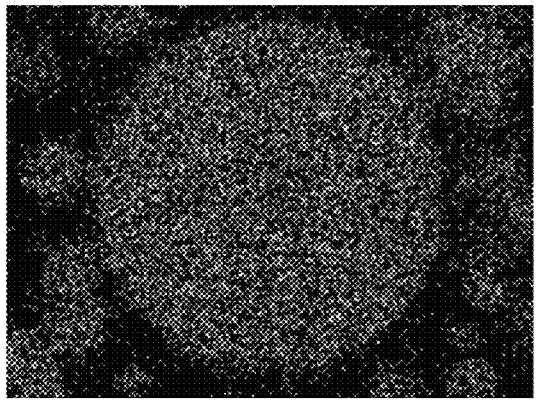

An example of the present invention is described in detail below, but the present invention is not limited to the following description, and modification may be suitably made without departing from the gist of the present invention.

1. Method for Producing Barium Sulfate Spherical Composite Powder

The method for producing a barium sulfate spherical composite powder of the present invention (also referred to simply as "composite powder") includes the steps of (1) preparing a slurry containing particulate barium sulfate and a silica sol, (2) spray-drying the slurry, and (3) firing a dry substance obtained in the step (2). The method may further contain one or more other steps as needed. Other steps are not limited. In the composite powder obtained by the production method, the silica presumably serves as a binder (bonding agent). The composite powder may be also referred to as granulated particles.

1) Step (1)

The following describes the step (1).

The step (1) is a step of preparing a slurry containing particulate barium sulfate and a silica sol. The slurry may be any one that contains particulate barium sulfate and a silica sol, which are preferably dispersed in a liquid medium. The liquid medium may be, but is not limited to, water or an organic solvent. The silica sol serves as a binder (also referred to as a binding agent). This leads to a composite of barium sulfate and silica through the steps (2) and (3) described below. The silica sol may be, but is not limited to, a commercial product (e.g., SNOWTEX ST-O available from Nissan Chemical Industries, Ltd.) or a synthesized product.

The solids concentration of the silica sol is preferably, but not limited to, 10 to 30% by mass, for example.

The particulate barium sulfate may be any one, and suitably has an average particle size of 0.005 to 0.25 µm, for example. Such particulate barium sulfate leads to a composite powder having higher strength, higher sphericity, and lower specific gravity. The average particle size is more preferably 0.01 to 0.25 µm.

Herein, the average particle size of the particulate barium sulfate in the slurry can be determined by the method described in the examples below.

The particulate barium sulfate may have any shape.

The particulate barium sulfate may be commercially available particulate barium sulfate (e.g., BARIFINE®, BF series available from Sakai Chemical Industry Co., Ltd., Bariclear® series available from Resino Color Industry Co., Ltd.), particulate barium sulfate obtained by reacting barium hydroxide and sulfuric acid, or particulate barium sulfate obtained by reacting a soluble barium salt (e.g., barium sulfide, barium chloride, barium nitrate) and sulfuric acid or a soluble sulfate (e.g., sodium sulfate, ammonium sulfate). In particular, particulate barium sulfate obtained by reacting barium hydroxide and sulfuric acid is suitable.

A barium source is preferably at least one selected from the group consisting of barium hydroxide, barium sulfide, and barium chloride as described above. In particular, the barium source is preferably barium chloride and/or barium hydroxide. Such a barium source gives high safety and much better texture to the composite powder.

To produce the particulate barium sulfate, the barium source and sulfuric acid or the soluble sulfate may be reacted at any pH, preferably reacted while the pH is kept within the range of 4 to 10, for example. With a pH within the range, generation of by-products such as soluble barium salts is sufficiently prevented. The slurry of particulate barium sulfate also preferably has a pH within the range. The pH is particularly preferably set to suit the barium source used as a raw material. For example, when the barium source is barium sulfide, pH is preferably 5 to 9, more preferably 6 to 8, when the barium source is barium hydroxide, pH is preferably 4 to 10, more preferably 5 to 8, and when the barium source is barium chloride, pH is preferably 5 to 10, more preferably 5 to 8.

The slurry containing particulate barium sulfate and a silica sol may be prepared by any method, and can be obtained by mixing a powder or slurry of particulate barium sulfate with a silica sol. For example, the method may be a method in which first a slurry of particulate barium sulfate is prepared, then a silica sol is added thereto, and they are mixed; a method in which a slurry of particulate barium sulfate is added to a silica sol, and they are mixed; or a method in which a powder of particulate barium sulfate and a silica sol are added to a liquid solvent, and they are mixed. When a slurry of particulate barium sulfate is used, it may be prepared by repulping with water commercially available particulate barium sulfate or particulate barium sulfate prepared by reacting the barium source and sulfuric acid or a soluble sulfate, filtering, washing with water, and drying the reaction product, for example. Alternatively, the slurry of particulate barium sulfate may be a slurry as it is obtained by reacting the barium source and sulfuric acid or a soluble sulfate. The concentration of the particulate barium sulfate in the slurry is preferably, but not limited to, 50 g/L to 200 g/L, for example.

The slurry containing particulate barium sulfate and a silica sol is suitably prepared so that the particulate barium sulfate and the silica in the slurry have a mass ratio ($BaSO_4$/$SiO_2$) of 99/1 to 55/45. With a mass ratio within the range, the strength of the composite powder is higher and the texture of the composite powder is better. The mass ratio is more preferably 95/5 to 70/30.

In the slurry, the total solids concentration of the barium sulfate and the silica is 30 g/L to 800 g/L. The composite powder can be produced to have high strength and good texture by spray-drying a slurry having such a concentration. The total solids concentration is more preferably 30 g/L to 400 g/L, still more preferably 50 g/L to 200 g/L.

The slurry containing particulate barium sulfate and a silica sol may have any viscosity, and preferably has a viscosity of 1 to 2000 mPa·s (20° C.), for example. The slurry having a viscosity within the range is more suitably spray-dried. The viscosity is preferably 1 to 1000 mPa·s, more preferably 10 to 900 mPa·s. A viscosity of the slurry higher than 2000 mPa·s is unfavorable because the dry substance obtained after spray-drying possibly have a shape which is not a spherical shape such as a shape having a concave.

Herein, the viscosity of the slurry can be determined with a B-type viscometer (Tokyo Keiki Inc.).

The slurry containing particulate barium sulfate and a silica sol may contain a dispersant as needed as long as the dispersant does not impair the effects of the invention. An example of the dispersant to be used is SN dispersant 5468 (San Nopco Limited). Although 0.1 to 2% by weight of the dispersant may be added to the slurry containing particulate barium sulfate and a silica sol, addition of no dispersant leads to a composite powder having better texture.

2) Step (2)

The following describes the step (2).

The step (2) is a step of spray-drying the slurry obtained in the step (1). Through the spray-drying, a spherical dry substance is obtained.

The spray-drying may be performed by any method. Suitably, the slurry is sprayed using a nozzle system such as a two-fluid or four-fluid nozzle system, or a rotary disc system. In the case of a rotary disc system, the rotation speed of the rotary disc is preferably, but not limited to, 15000 to 25000 rpm. The inlet temperature and the outlet temperature may be any temperature. Preferably, the inlet temperature is at least 200° C. and lower than 400° C., and the outlet temperature is at least 90° C. (more preferably 90° C. to 140° C.)

The dry substance obtained in the step (2) is preferably in the form of spherical particles. It may be in the form of flocculate or aggregate of primary particles.

The production method of the present invention easily achieves spheroidizing. The reason for this is as follows.

Regarding the zeta potential in a neutral solution, it is common that barium sulfate is positively charged and silica is negatively charged. The barium sulfate and the silica attract each other with great force. Thus, the slurry obtained in the step (1) tends to be in the aggregation state, that is, the particles are likely to be aggregated. The slurry which tends to be in the aggregation state is less affected by movement of the liquid due to the evaporation of the solvent during spray-drying in the step (2). Thus, the slurry easily undergoes spheroidization. Such easy spheroidization is presumably one factor for good texture of the composite powder obtained through the step (3).

3) Step (3)

The following describes the step (3).

The step (3) is a step of firing the dry substance obtained in the step (2).

The firing temperature is preferably, but not limited to, 200° C. to 1100° C. The primary particles of the composite powder fired at such a temperature are sintered to give a denser composite powder having high strength. For preventing uneven firing, the firing is suitably performed with uniform temperature distribution. In particular, the firing temperature is preferably 300° C. or higher for further increasing the strength. The firing temperature is more preferably 400° C. or higher. The firing temperature is preferably 1000° C. or lower for further preventing melt bonding of the composite powder. The firing temperature is particularly preferably 400° C. to 1000° C. At such a firing temperature, the effects of the present invention are further achieved.

The firing time is preferably 0.5 to 12 hours, for example. The primary particles of the composite powder fired for such a time are sufficiently sintered to give a denser composite powder having high strength. Even if the firing is performed for longer than 12 hours, the effects proportional to the firing time cannot be obtained, and the productivity may not further increase. The firing time is more preferably 0.5 to 5 hours.

The term "firing temperature" as used herein means the highest temperature reached in the firing. The term "firing time" means a retention time at the highest temperature reached in the firing, which excludes the temperature rise time, i.e., the time required to reach the highest temperature. The temperature rise time is not limited, and suitably as short as possible.

The firing may be performed by any method, and may be performed by fluidized-bed firing or fixed-bed firing, for example. The firing may be performed in any atmosphere, and may be performed in an air atmosphere or an inert gas atmosphere such as nitrogen or argon atmosphere.

In the production method, the step (3) (firing step) may be repeated multiple times as needed. When the firing step is repeated multiple times, the total firing time preferably falls within the above-described preferred range of the firing time.

The final product (composite powder) obtained through the step (3) may be in the form of spherical particles. These particles may be in the form of flocculate or aggregate of the primary particles.

2. Barium Sulfate Spherical Composite Powder

The barium sulfate spherical composite powder of the present invention is a spherical composite powder of barium sulfate and silica, and has an average particle size of 0.5 to 100 μm, a haze of 50% or more, and a silica content of 1 to 45% by mass. The spherical composite powder can be easily and simply produced by the above-described production method of the present invention.

The composite powder has an average particle size of 0.5 to 100 μm. The composite powder having an average particle size within the range is easily handled and has excellent texture and smoothness, and thus is useful for various applications. In particular, when the composite powder having an average particle size within the range is used for a product directly in contact with the skin, such as a cosmetic product, the product applied to the skin provides neither friction nor rough texture, leading to good texture. The average particle size is preferably 1 to 50 μm, more preferably 1 to 30 μm.

Hereinafter, the average particle size of the powder refers to a 50% cumulative particle diameter on the volume basis. In other words, the average particle size means a diameter (D50) at which the amount of the particles having larger diameters than this diameter is equal to the amount of the particles having smaller diameters than this diameter when the powders are divided into two by a certain diameter. Specifically, D50 is determined by the method described in the examples below.

The composite powder has a haze of 50% or more. The haze within the range is suitable because a cosmetic product containing the composite powder exhibits a high soft focus effect. The haze is preferably 55% or more, more preferably 60% or more.

The haze as used herein can be determined by the method described in the examples below.

The composite powder preferably has a total light transmittance of 90% or higher. The composite powder having a total light transmittance within the range provides transparency while exhibiting a high soft focus effect. The total light transmittance is more preferably 91% or higher.

Herein, the total light transmittance can be determined by the method described in the examples below.

The composite powder has a silica content of 1 to 45% by mass. The composite powder having a silica content within the range sufficiently exhibits the effects of silica and barium sulfate, and thus has suitable physical properties such as strength, texture, total light transmittance, and haze. The silica content is preferably 5 to 30% by mass.

Herein, the silica content of the composite powder can be determined by the method described in the examples below.

The composite powder also preferably has a sphericity of 1.0 to 1.5. With such a sphericity, much better texture and smoothness are obtained. The sphericity is more preferably 1.3 or less, still more preferably 1.2 or less, particularly preferably 1.1 or less.

Herein, the sphericity can be determined by the method described in the examples below. The high sphericity means that the powder is almost spherical, that is, the sphericity is closed to 1.0.

The rate of change in D50 of 1 g of the composite powder from before to after the composite powder is crushed with an electric mortar (for 10 minutes at a rotation speed of 150 rpm) is preferably within ±30%. The expression "the rate of change is within ±30%" means that the spherical shape can be sufficiently maintained even if an extremely large external impact is applied to the composite powder by crushing it in an electric mortar for 10 minutes at a rotation speed of 150 rpm. Such a powder has extremely high particle strength, and thus does not break when it is rubbed into the skin for a long time, leading to lasting good texture. The rate of change is more preferably ±20% or lower, still more preferably ±15% or lower, particularly preferably ±10% or lower.

Herein, the conditions of crushing with an electric mortar are described in detail in the examples below.

The composite powder also preferably contains a layer surface-treated with a water-repellent organic compound.

The surface treatment with a water-repellent organic compound refers to water repellent treatment for reducing the affinity of the surfaces of the composite powder to water. Specifically, this treatment is to prevent occurrence of precipitation and turbidity before addition of isopropyl alcohol (only in water) in the below-described water repellency test method.

Examples of the water-repellent organic compound include organic silicon compounds, organic aluminum compounds, organic titanium compounds, higher fatty acids, metal soaps, polyols, and alkanolamines. Two or more of the compounds may be used for surface treatment.

Specific preferred examples of the water-repellent organic compound include silicone oils such as hydrogen dimethicone and triethoxysilylethyl polydimethylsiloxyethyl hexyl dimethicone; alkyl silanes such as trialkoxyoctylsilane and trialkoxydecylsilane; silane coupling agents such as vinyl trialkoxysilane, 3-glycosidoxypropyltrialkoxysilane, 3-methacryloxypropylmethyldialkoxysilane, 3-aminopropyltrialkoxysilane, and 3-mercaptopropylmethyldialkoxysilane; and metal salts of C12-C18 fatty acids such as stearic acid, isostearic acid, myristic acid, palmitic acid, and palm oil fatty acid. Examples of the metal salts of the fatty acid metal salts include lithium, sodium, potassium, magnesium, calcium, barium, zinc, and aluminum, and calcium and magnesium are particularly preferred.

The water-repellent organic compound is preferably a compound capable of having any chemical bond with the composite powder, or may be a compound capable of physically adsorbing to the composite powder.

The surface treatment with a water-repellent organic compound gives further improved texture to the powder, and the resulting powder is blended well with oily agents when it is incorporated in a cosmetic product, for example.

The amount of the water-repellent organic compound used for treatment is preferably 0.1 to 10% by weight, more preferably 0.5 to 8% by weight relative to the barium sulfate spherical composite powder. If the amount is less than 0.1% by weight, the water repellency is insufficient. If the amount is more than 10% by weight, the cost increases and the effects proportional to the amount may not be obtained.

The treatment with a water-repellent organic compound may be performed by any method. For example, it may be performed by mixing in a dry process with a mixer.

3. Applications

The barium sulfate spherical composite powder of the present invention has significantly high strength and excellent texture and achieves high haze while maintaining high total light transmittance. Thus, it is preferably incorporated in cosmetic products, medicines, quasi-drugs, radiation shielding materials, coating materials, resin materials, catalysts, toners for printing, lubricants, and other products. In particular, it is suitably incorporated in cosmetic products. The present invention also relates to a cosmetic product containing the above composite powder.

4. Cosmetic Product

The following describes the cosmetic product containing the barium sulfate spherical composite powder of the present invention.

The cosmetic product of the present invention containing the composite powder achieves very good texture. Specifically, it provides good smoothness and light texture and does not break when it is rubbed into the skin for a long time, leading to lasting good texture. It is also expected to achieve a soft focus effect and a sebum adsorbing effect. Non-limiting examples of the cosmetic product include a foundation, a makeup base, an eye shadow, a blusher, a mascara, a lipstick, a sunscreen agent, and an oil-absorbing sheet, with a foundation being particularly suitable.

EXAMPLES

The present invention will be described in detail with reference to examples below. The present invention should not be limited to these examples. The physical properties were evaluated as follows.

1. Average Particle Size of Particulate Barium Sulfate in Slurry

The average particle size (D50: a particle size at which the cumulative volume constitutes 50% of the total particle volume in a particle size distribution) of the particulate barium sulfate used to prepare the slurry containing particulate barium sulfate and a silica sol was measured with a laser diffraction/scattering particle size distribution measuring device (LA-950 available from Horiba, Ltd.) (flow type, solvent: 0.025% by mass aqueous sodium hexametaphosphate solution, internal ultrasonic irradiation: 40 W, 30 seconds).

2. Physical Properties of Powder

1) Average Particle Size

The average particle size (D50) was measured with a laser diffraction/scattering particle size distribution measuring device (LA-950 available from Horiba, Ltd.) (flow type, solvent: 0.025% by mass aqueous sodium hexametaphosphate solution, internal ultrasonic irradiation: 40 W, 30 seconds).

2) SiO$_2$ Content (Fluorescent X-Ray/Calibration Curve Method)

A glass bead was formed in advance from a standard substance (for use in calibration curve) whose SiO$_2$ concentration was known.

Separately, 0.6 g of a sample and 5.4 g of a flux (lithium tetraborate anhydride) were mixed, and the mixture was fused at 1000° C. for 200 seconds to form a 10-fold diluted glass bead sample.

The glass bead sample was subjected to measurement with a X-ray fluorescence spectrometry (ZSX Primus II available from Rigaku Corporation) by a calibration curve method. The resulting value was multiplied by 10 (dilution factor) to give a SiO$_2$ content of the sample according to the following formula (1).

$$SiO_2 \text{ content} = \text{Measured value} \times \text{Dilution factor} \qquad (1)$$

3) Haze, Total Light Transmittance

The haze and the total light transmittance of the powder (also referred to as a sample) were determined according to the following procedures.

(1) 0.5 g of a sample and 4.5 g of Shin-Etsu Silicone® KF-96A-5000CS (Shin-Etsu Chemical Co., Ltd.) were put into an ointment jar and briefly mixed with, for example, a spatula.

(2) The mixture obtained in the step (1) was stirred in Awatori Rentaro® ARE-250 (Thinky Corporation) at 2000 rpm for five minutes.

(3) The mixture obtained in the step (2) was applied to a 10 cm×10 cm glass sheet using an applicator to form a film having a thickness of 1 mil (25.4 μm).

(4) The haze and the total light transmittance of the film obtained in the step (3) were each measured three times with a haze meter (Haze Meter NDH4000 available from Nippon Denshoku Industries Co., Ltd.). The three values of each of the haze and the total light transmittance obtained by the measurements were averaged. The resulting average values were used as a "haze" and a "total light transmittance" in the examples.

4) Strength

The strength of the powder (sample) was determined according to the following procedures.

(1) 1 g of a sample was crushed in an electric mortar (MMPS-T1 available from AS ONE Corporation) at a rotation speed of 150 rpm for 10 minutes.

(2) 0.1 g of the crushed product obtained in the step (1) was put in a 150-mL polypropylene cup, and 50 mL of an aqueous sodium hexametaphosphate solution (0.025% by mass) was put therein. The contents were exposed to ultrasonic irradiation (300 μA) for one minute with an ultrasonic homogenizer (US-600 available from Nippon Seiki Co., Ltd.).

(3) The liquid obtained in the step (2) was subjected to measurement of D50 with a laser diffraction/scattering particle size distribution measuring device (LA-950 available from Horiba, Ltd.) (flow type, solvent: 0.025% by mass aqueous sodium hexametaphosphate solution, internal ultrasonic irradiation: 40 W, 30 seconds). The sample before crushing was also subjected to measurement of D50 similarly with the measuring device.

(4) The rate of change in D50 of the sample was determined from D50 (D50$_A$) of the sample after crushing and D50 (D50$_B$) of the sample before crushing according to the following equation (2). The rate of change (%) was defined as "strength." That is, a lower rate of change indicates a smaller change due to crushing, and thus indicates high strength.

[Equation 1]

$$\text{Rate of change } (\%) = \frac{D50_B - D50_A}{D50_B} \times 100 \qquad (2)$$

5) Texture (Sensory Test)

The texture of the powder (sample) was evaluated by ten panelists on a scale of 1 to 5 (5 is the best). The test was performed by touching the powder by the back of the hand and the index finger. The resulting scores were averaged.

A score of 5 indicates the case where "a powder easily glides on the skin and provides smoothness," and a score of 1 indicates the case where "a powder does not glide and does not provide smoothness."

6) Observation of Particle

The shapes of the respective particles were observed with a field emission scanning electron microscope (JSM-7000F available from JEOL). For the powder obtained in Experimental Example 1, the cross sections of the respective particles were also observed.

7) Sphericity

A diagonal line was drawn on an image taken with a field emission scanning electron microscope (JSM-7000F available from JEOL), and the major axes and minor axes of 50 particles on the line were determined. The values of the "major axis/minor axis" of the respective particles were averaged to determine the sphericity.

8) Water Repellency

A 500-mL beaker was charged with 300 mL of ion exchange water. While the ion exchange water was stirred at a speed of 250 rpm, 1 g of a sample barium sulfate spherical composite powder was put thereinto. The contents were stirred at the same speed for one minute. After the stirring was stopped, the degree of turbidity of the ion exchange water in the beaker was visually observed. The case where precipitation and turbidity did not occur was evaluated as "good" and the case where precipitation or turbidity occurred was evaluated as "poor." A sample evaluated as "good" was again tested in a liquid mixture of 5 mL of isopropyl alcohol and 295 mL of ion exchange water by the same procedures. Until the sample was evaluated as "poor," the same test was repeated with increasing the amount of isopropyl alcohol by 5 mL and with decreasing the amount of ion exchange water by 5 mL so that the amount of the liquid mixture was kept constant at 300 mL. The amount of isopropyl alcohol used in the test in which the sample was finally evaluated as "poor" was designated as an indicator of water repellency. The larger the amount of isopropyl alcohol used in the test in which the sample was finally evaluated as "poor," the better the water repellency of the sample barium sulfate spherical composite powder.

Experimental Example 1

First, 3 L of a 0.58 mol/L aqueous barium hydroxide solution and 3 L of 0.58 mol/L dilute sulfuric acid were simultaneously introduced into a reaction vessel while the pH was maintained at 7 to 10 to give a slurry of 68 g/L particulate barium sulfate (the average particle size of the particulate barium sulfate in the slurry is shown in Table 1). To the slurry was added 418 g of a silica sol ($BaSO_4$/ $SiO_2$=83/17) (SNOWTEX ST-O available from Nissan Chemical Industries, Ltd., solids concentration: 20% by mass), and they were mixed to give a slurry containing barium sulfate and silica in a total solids concentration of 77 g/L.

The slurry was spray-dried with a spray dryer (MDL-050 available from Fujisaki Electric Co., Ltd.) with an inlet temperature of 215° C. and an outlet temperature of 105° C. The resulting dry substance was fired in the air at the temperature and for the time shown in Table 1 to give a barium sulfate spherical composite powder.

The water repellency of the barium sulfate spherical composite powder was tested by the above-described method. The barium sulfate spherical composite powder dispersed in water (only) caused turbidity before addition of isopropyl alcohol. Thus, it was found to have no water repellency.

Experimental Examples 2 to 4, 6

Barium sulfate spherical composite powders were prepared as in Experimental Example 1, except that the amount of the silica sol and/or the firing conditions were/was changed according to Table 1.

Experimental Example 5

Spherical barium sulfate was prepared as in Experimental Example 1, except that no silica sol was added and the firing conditions were changed according to Table 1.

Experimental Example 7

A composite powder of barium sulfate and alumina was prepared as in Experimental Example 2, except that an alumina sol (alumina sol-10A available from Kawaken Fine Chemicals Co., Ltd., solids concentration: 9.7 to 10.3% by mass) was used instead of a silica sol.

Experimental Example 8

First, 23.5 g of trisodium citrate dihydrate and 17.1 g of barium chloride dihydrate were put into a 20-L stainless steel cylindrical pot. They were dissolved in pure water added to the pot up to a volume of 5 L (the resulting solution was referred to as a solution A). Separately, 9.9 g of sodium sulfate anhydride was put into a 10-L stainless steel cylindrical pot. It was dissolved in pure water added to the pot up to a volume of 5 L (the resulting solution was referred to as a solution B).

The total amount of the solution B was added to the solution A under stirring within 10 seconds, and they were stirred for one hour. The resulting liquid was filtered, washed, and dried at 100° C. to give a spherical barium sulfate powder.

The physical properties of the respective powders obtained in Experimental Examples 1 to 8 were evaluated. The results are shown in Table 1 and FIGS. 1 and 2. Each of the powders obtained in Experimental Examples 2, 5, and 6 in an amount of 1 g was crushed with an electric mortar (MMPS-T1 available from AS ONE Corporation) at a rotation speed of 150 rpm for 10 minutes. The crushed substance was observed with a field emission scanning electron microscope (JSM-7000F available from JEOL) (see FIG. 3).

TABLE 1

| | Item | Unit | Experimental Example 1 | Experimental Example 2 | Experimental Example 3 | Experimental Example 4 | Experimental Example 5 | Experimental Example 6 | Experimental Example 7 | Experimental Example 8 |
|---|---|---|---|---|---|---|---|---|---|---|
| Particulate barium sulfate | Production method of particle | — | Barium hydroxide-sulfuric acid method | | | | | | | — |
| | Average particle size | nm | 89 | 89 | 89 | 86 | 86 | 89 | 85 | — |
| Oxide sol | Product name | — | SNOWTEX ST-O | SNOWTEX ST-O | SNOWTEX ST-O | SNOWTEX ST-O | — | SNOWTEX ST-O | Alumina sol –10A | — |
| | Mass ratio in slurry ($BaSO_4/SiO_2$) | — | 83/17 | 83/17 | 70/30 | 95/5 | — | 83/17 | 83/17* | — |
| Solids ($BaSO_4 + SiO_2$) concentration of slurry for spray-drying | | g/L | 77 | 77 | 86 | 70 | — | 77 | — | — |
| Drying method | | | Spray-drying | Spray-drying | Spray-drying | Spray-drying | Spray-drying | Spray-drying | Spray-drying | — |
| Firing temperature/ Firing time | | ° C. × h | 400 × 2 | 900 × 1 | 900 × 1 | 900 × 1 | 680 × 1 | 250 × 2 | 900 × 1 | — |
| Physical properties of powder | Average particle size | μm | 2.68 | 2.47 | 3.06 | 2.63 | 3.31 | 2.69 | 3.42 | 0.8 |
| | $SiO_2$ content | % by mass | 17.1 | 17.3 | 30.7 | 4.5 | N.D. | 16.9 | — | N.D. |
| | Haze | % | 60.26 | 62.3 | 64.42 | 66.08 | 55.99 | 60.26 | 70.13 | 43.75 |
| | Total light transmittance | % | 92.62 | 92.615 | 92.76 | 91.59 | 87.51 | 92.62 | 91.56 | 90.35 |
| | Strength (rate of change) | % | 8.5 | 1.9 | 1.4 | 1.4 | 74.7 | 16.1 | 8.2 | — |
| | Touch feeling | — | 3.3 | 4.7 | 3.8 | 3.6 | 3 | 3 | 2.1 | 4.8 |
| | Sphericity | — | — | — | 1.08 | — | — | — | — | — |

In Table 1, the mass ratio marked with * refers to the mass ratio in the slurry ($BaSO_4/Al_2O_3$).

Experimental Example 9

First, 0.15 g of triethoxysilylethyl polydimethylsiloxyethyl hexyl dimethicone (KF-9909 available from Shin-Etsu Chemical Co., Ltd.) was diluted with 2 g of hexane, and then the dilution was mixed with 4.85 g of the barium sulfate spherical composite powder obtained in Experimental Example 1. After the hexane was dried off at room temperature, the mixture was heated with a dryer set at 150° C. to give a silicone-treated barium sulfate spherical composite powder.

The water repellency of the powder was tested by the above-described method. The result was that the powder was evaluated as "poor" when the amount of isopropyl alcohol reached 80 ml in 300 ml of the mixture.

Experimental Example 10

First, 0.15 g of trialkoxyoctylsilane (OFS-6341 available from Dow Corning Toray Co., Ltd.) was diluted with 2 g of hexane, and then the dilution was mixed with 4.85 g of the barium sulfate spherical composite powder obtained in Experimental Example 1. After the hexane was dried off at room temperature, the mixture was heated with a dryer set at 120° C. to give a silane coupling agent-treated barium sulfate spherical composite powder.

The water repellency of the powder was tested by the above-described method. The result was that the powder was evaluated as "poor" when the amount of isopropyl alcohol reached 50 ml in 300 ml of the mixture.

Figure 2:
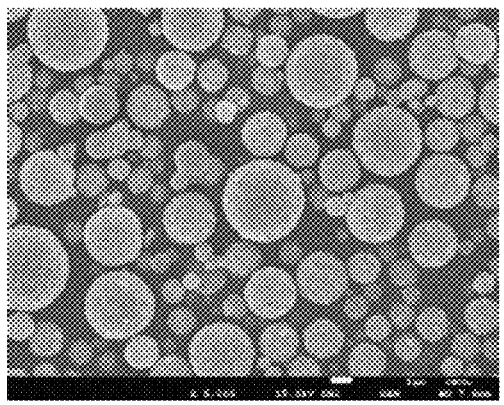
FIG. 2 illustrates SEM images of powders obtained in Experimental Examples 2, 4 to 8. The SEM images for Experimental Examples 2, 4 to 7 are taken at a magnification of 5000, and the SEM image for Experimental Example 8 is taken at a magnification of 10000.
Figure 2:
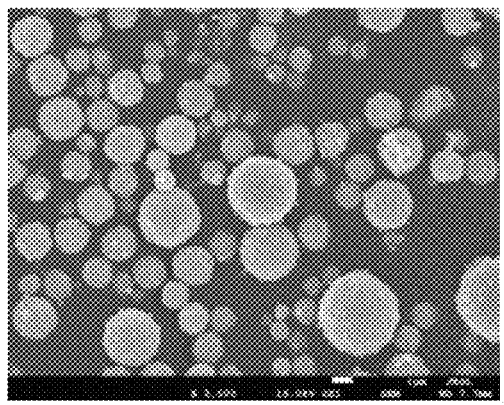
Figure 2:
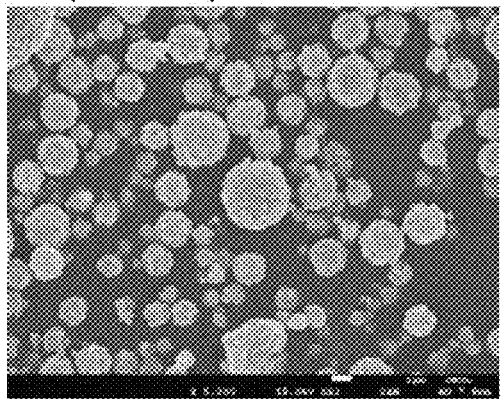
Figure 2:
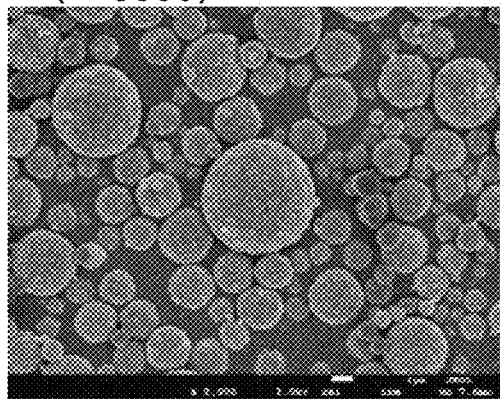
Figure 2:
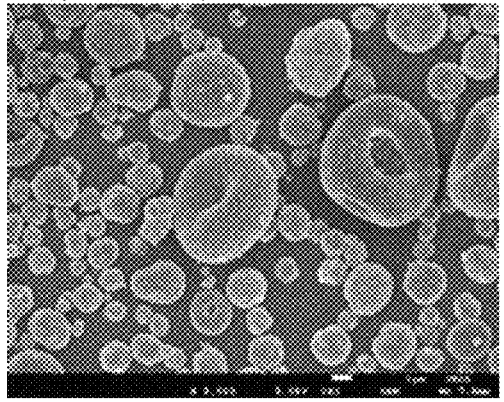
Figure 2:
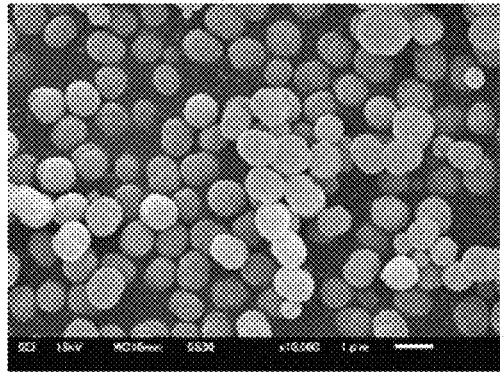

Table 1 and FIGS. 1 and 2 confirm the following matters.

In Experimental Examples 1 to 4, and 6, spherical composite powders containing barium sulfate and silica are prepared by the production method of the present invention including the steps of (1) preparing a slurry containing particulate barium sulfate and a silica sol, (2) spray-drying the slurry, and (3) firing a dry substance obtained in the step (2). Unlike these examples, Experimental Example 5 does not use a silica sol, Experimental Example 7 uses an alumina sol instead of a silica sol, and Experimental Example 8 does not include the steps (1) and (2). These examples differ from the production method of the present invention in these points.

Comparison of the physical properties of these powders having such differences shows that the strength, total light transmittance, and haze of the respective composite powders obtained in Experimental Examples 1 to 4, and 6 are all higher than those of the powder (spherical barium sulfate) obtained in Experimental Example 5 (see Table 1). In particular, the strength is significantly better. The powder (composite powder of barium sulfate and alumina) obtained in Experimental Example 7 fails to be spherical, resulting in poor texture (see FIG. 2(e) and Table 1), and the powder obtained in Experimental Example 8 has high total light transmittance, but has low haze (see Table 1). Thus, the production method of the present invention is found to provide a barium sulfate spherical composite powder having significantly high strength and excellent texture and achieving high haze while maintaining high total light transmittance. In addition, comparison of Experimental Examples 1 to 4 with Experimental Example 6 demonstrates that the composite powders obtained through firing at a temperature of preferably 300° C. or higher (more preferably 400° C. or higher) (Experimental Examples 1 to 4) have much higher strength and much better texture (see Table 1).

Figure 3:
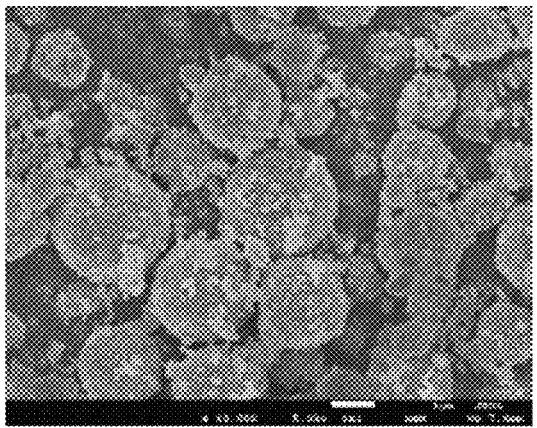
FIG. 3 illustrates SEM images of the powders obtained in Experimental Examples 2, 5 and 6 after crushing with a mortar, which are taken at a magnification of 10000.
Figure 3:
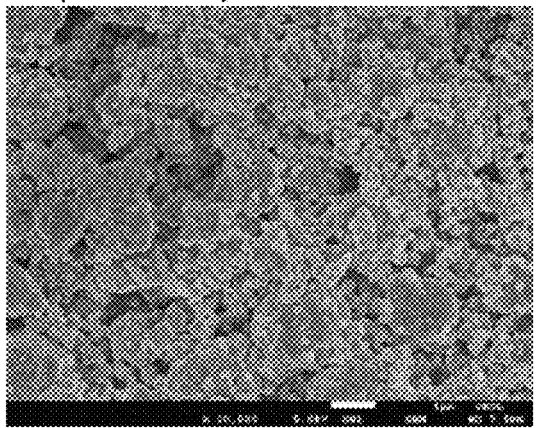
Figure 3:
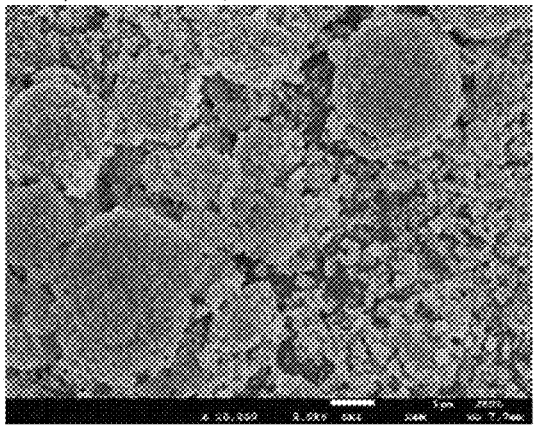

FIG. 3 confirms the following matters.

The production methods of Experimental Examples 2 and 5 differ only in whether the step (1) is conduced or not. When a very large external impact (mortar crush) was applied to the respective powders obtained in these examples having such a difference, the powder obtained in Experimental Example 2 remained spherical, whereas the powder obtained in Experimental Example 5 could not remain spherical (see the images (a) and (b) in FIG. 3). The powder obtained in Experimental Example 6, which was produced through firing at a temperature lower than that in Experimental Example 2, has been found to contain particles having a more spherical shape than the powder obtained in Experimental Example 5, but contain some slightly broken or deformed particles (see FIG. 3(c)). Accordingly, the production method of the present invention is capable of providing a spherical composite powder having extremely high strength. In particular, a composite powder produced through firing at a temperature of preferably 300° C. or higher (more preferably 400° C. or higher) has much higher strength.

The invention claimed is:

1. A method for producing a barium sulfate spherical composite powder, which is a method for producing a spherical composite powder of barium sulfate and silica, the method comprising the steps of:
   (1) preparing a slurry containing particulate barium sulfate and a silica sol;
   (2) spray-drying the slurry; and
   (3) firing a dry substance obtained in the step (2).

2. The method according to claim 1,
   wherein the particulate barium sulfate and the silica in the slurry have a mass ratio ($BaSO_4/SiO_2$) of 99/1 to 55/45.

3. The method according to claim 1,
   wherein the firing in the step (3) is performed at a firing temperature of 400° C. to 1000° C.

4. A barium sulfate spherical composite powder which is a spherical composite powder comprising barium sulfate and silica,
   the composite powder having
   an average particle size of 0.5 to 100
   a haze of 50% or more,
   a silica content of 1 to 45% by mass, and
   a sphericity of 1.0 to 1.5.

5. The barium sulfate spherical composite powder according to claim 4,
   wherein the composite powder contains a layer surface-treated with a water-repellent organic compound.

6. A cosmetic product comprising the barium sulfate spherical composite powder according to claim 4.

* * * * *